(12) United States Patent
Garbus et al.

(10) Patent No.: US 11,116,601 B2
(45) Date of Patent: *Sep. 14, 2021

(54) SURGICAL CANNULAS AND RELATED SYSTEMS AND METHODS OF IDENTIFYING SURGICAL CANNULAS

(71) Applicant: INTUITIVE SURGICAL OPERATIONS, INC., Sunnyvale, CA (US)

(72) Inventors: Brandon R. Garbus, Santa Clara, CA (US); Allen C. Thompson, Los Altos, CA (US); Justin Krom, Southington, CT (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/871,805

(22) Filed: May 11, 2020

(65) Prior Publication Data

US 2020/0268479 A1    Aug. 27, 2020

Related U.S. Application Data

(63) Continuation of application No. 16/221,994, filed on Dec. 17, 2018, now Pat. No. 10,682,205, which is a
(Continued)

(51) Int. Cl.
*G06K 19/06* (2006.01)
*A61B 90/98* (2016.01)
(Continued)

(52) U.S. Cl.
CPC .......... *A61B 90/98* (2016.02); *A61B 17/3403* (2013.01); *A61B 17/3476* (2013.01);
(Continued)

(58) Field of Classification Search
CPC ........ G06K 7/084; G06K 7/085; G06K 7/087; A61B 90/90; A61B 90/96; A61B 90/98; G06Q 10/087; G06Q 50/22
(Continued)

(56) References Cited

U.S. PATENT DOCUMENTS

| 5,269,794 A | 12/1993 | Rexroth |
| RE34,556 E | 3/1994 | Sjostrom et al. |

(Continued)

FOREIGN PATENT DOCUMENTS

| CN | 1706348 A | 12/2005 |
| CN | 101242788 A | 8/2008 |

(Continued)

OTHER PUBLICATIONS

Allegro, A1171: Micropower Ultrasensitive Hall Effect Switch, Rev. 5, Oct. 2011, 10 pages.
(Continued)

*Primary Examiner* — Daniel St. Cyr
(74) *Attorney, Agent, or Firm* — Jones Robb, PLLC

(57) ABSTRACT

A method includes sensing magnet information at a plurality of magnet positions on a cannula and determining identification information for the cannula based on the magnet information.

25 Claims, 11 Drawing Sheets

Related U.S. Application Data continuation of application No. 15/126,903, filed as application No. PCT/US2015/020913 on Mar. 17, 2015, now Pat. No. 10,172,687.

(60) Provisional application No. 61/954,318, filed on Mar. 17, 2014.

(51) Int. Cl.

| | | |
|---|---|---|
| *A61B 34/30* | (2016.01) | |
| *A61B 34/00* | (2016.01) | |
| *A61B 34/35* | (2016.01) | |
| *A61B 46/10* | (2016.01) | |
| *A61B 17/34* | (2006.01) | |
| *G06K 7/08* | (2006.01) | |
| *A61B 90/90* | (2016.01) | |
| *A61B 17/00* | (2006.01) | |

(52) U.S. Cl.
CPC ............. *A61B 34/25* (2016.02); *A61B 34/30* (2016.02); *A61B 34/35* (2016.02); *A61B 46/10* (2016.02); *G06K 7/084* (2013.01); *A61B 17/3421* (2013.01); *A61B 90/90* (2016.02); *A61B 2017/00039* (2013.01); *A61B 2017/00876* (2013.01)

(58) Field of Classification Search
USPC ........................................ 235/449, 493, 435
See application file for complete search history.

(56) References Cited

U.S. PATENT DOCUMENTS

| | | | |
|---|---|---|---|
| 5,749,885 A | 5/1998 | Sjostrom et al. | |
| 6,037,724 A | 3/2000 | Buss et al. | |
| 7,666,191 B2 | 2/2010 | Orban, III et al. | |
| 7,900,805 B2 | 3/2011 | Shelton et al. | |
| 8,035,487 B2 | 10/2011 | Malackowski | |
| 8,182,469 B2 | 5/2012 | Anderson et al. | |
| 8,545,515 B2 | 10/2013 | Prisco et al. | |
| 8,568,391 B2 | 10/2013 | Kerns et al. | |
| 9,099,939 B2 | 8/2015 | Jungnickel et al. | |
| 9,532,849 B2 | 1/2017 | Anderson et al. | |
| 10,172,687 B2 * | 1/2019 | Garbus ................. G06K 7/084 |
| 10,682,205 B2 * | 6/2020 | Garbus ............. A61B 17/3476 |
| 2010/0081875 A1 | 4/2010 | Fowler et al. | |
| 2013/0325031 A1 | 12/2013 | Schena et al. | |
| 2013/0325033 A1 | 12/2013 | Schena et al. | |
| 2013/0325034 A1 | 12/2013 | Schena et al. | |
| 2019/0192254 A1 | 6/2019 | Garbus et al. | |

FOREIGN PATENT DOCUMENTS

| | | |
|---|---|---|
| CN | 101632610 A | 1/2010 |
| EP | 1439026 A1 | 7/2004 |
| JP | H05184690 A | 7/1993 |
| JP | 2000507839 A | 6/2000 |
| JP | 2007029274 A | 2/2007 |
| JP | 2007290096 A | 11/2007 |
| JP | 2012210294 A | 11/2012 |
| WO | WO-03024754 A1 | 3/2003 |
| WO | WO-2006104929 A2 | 10/2006 |
| WO | WO-2007041094 A1 | 4/2007 |
| WO | WO-2013075205 A1 | 5/2013 |
| WO | WO-2015127231 A1 | 8/2015 |

OTHER PUBLICATIONS

Diodes Inc, AH1892: Programmable Micropower Omnipolar Hall-effect Sensor Switch, Rev. 1-2, Document No. DS35092, May 2012, 11 pages.
Extended European Search Report for Application No. 15764215.8, dated Oct. 10, 2017, 10 pages.
Extended European Search Report for Application No. EP20155224.7 dated Apr. 6, 2020, 8 pages.
International Search Report and Written Opinion for Application No. PCT/US15/20913, dated Jun. 19, 2015, 16 pages.
Office Action and Search Report dated Jun. 25, 2018 for Chinese Application No. 201580014404.9 filed Mar. 17, 2015, 20 pages, with English translation prepared by Chinese patent law firm.
Rohm Semiconductor: Unipolar detection Hall ICs, Rev. C, Aug. 2010, 19 Pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

SURGICAL CANNULAS AND RELATED SYSTEMS AND METHODS OF IDENTIFYING SURGICAL CANNULAS

CROSS-REFERENCE TO RELATED APPLICATIONS

This application is a continuation of U.S. patent application Ser. No. 16/221,994, filed Dec. 17, 2018, which is a continuation of U.S. patent application Ser. No. 15/126,903, filed Sep. 16, 2016 (now U.S. Pat. No. 10,172,687), which is a national stage application of Intl App. No. PCT/US2015/020913, filed Mar. 17, 2015, which claims the benefit of U.S. Provisional Application No. 61/954,318, filed on Mar. 17, 2014, each of which is incorporated by reference herein in its entirety.

TECHNICAL FIELD

Aspects of the present disclosure relate to surgical cannulas, and related systems and methods of identifying surgical cannulas.

INTRODUCTION

Remotely controlled surgical instruments, which can include teleoperated surgical instruments as well as manually operated (e.g., laparoscopic, thorascopic) surgical instruments, are often used in minimally invasive medical procedures. During surgical procedures, a surgical instrument that extends through a cannula inserted into a patient's body and be remotely manipulated to perform a procedure at a surgical site. For example, in a teleoperated surgical system, cannulas and surgical instruments can be mounted at manipulator arms of a patient side cart and be remotely manipulated via teleoperation at a surgeon console. Cannulas may have differing configurations that are useful to various types of surgical procedures. While these various cannula configurations have been useful and effective for surgical procedures, still further improvements upon cannulas and the surgical systems that use them would be desirable, including improvements for automatically identifying a cannula.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a cannula for a surgical system comprises a magnet located in a position to be sensed by the surgical system in a mounted position of the cannula to the surgical system. At least one of a presence of the magnet and a polarity of the magnet is sensed in the mounted position of the cannula to provide identification information relating to the cannula.

In accordance with at least one exemplary embodiment, a patient side cart for a teleoperated surgical system comprises a base, a main column, and an arm connected to the main column. The arm may comprise a mount to receive a cannula and a reader to sense a magnet of an identification device in the cannula so as to receive identification information relating to a mounted cannula.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

DETAILED DESCRIPTION

Figure 1:
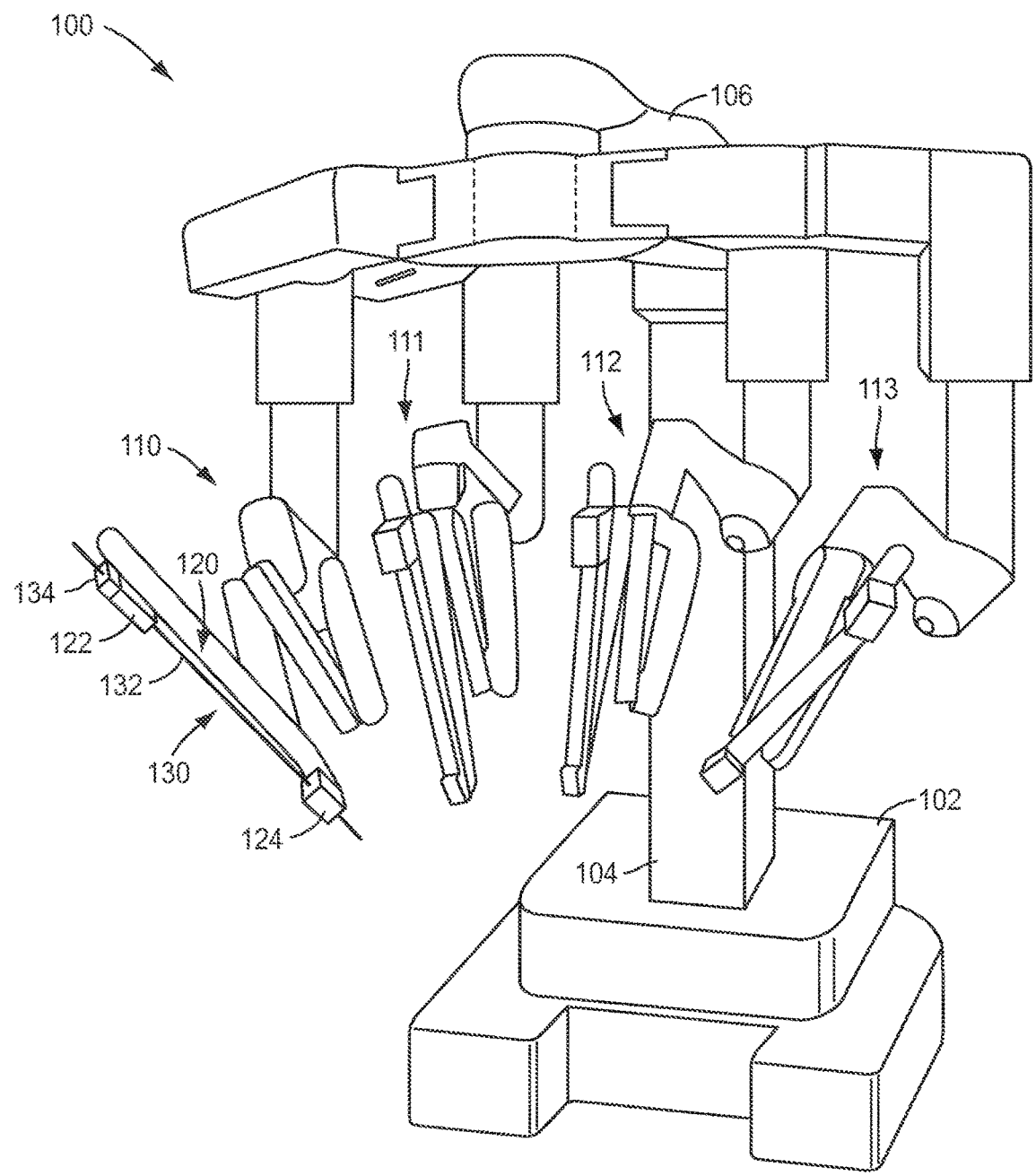
FIG. 1 is a perspective view of a patient side cart, according to an exemplary embodiment.

This description and the accompanying drawings that illustrate exemplary embodiments should not be taken as limiting. Various mechanical, compositional, structural, electrical, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural reference unless expressly and unequivocally limited to one reference. As used herein, the term "include" and its grammatical variants are intended to be non-limiting, such that recitation of items in a list is not to the exclusion of other like items that can be substituted or added to the listed items.

Further, this description's terminology is not intended to limit the disclosure or claims. For example, spatially relative terms—such as "beneath", "below", "lower", "above", "upper", "proximal", "distal", and the like—may be used to describe one element's or feature's relationship to another element or feature as illustrated in the orientation of the figures. These spatially relative terms are intended to encompass different positions (i.e., locations) and orientations (i.e., rotational placements) of a device in use or operation in addition to the position and orientation shown in the figures. For example, if a device in the figures is inverted, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. The relative proximal and distal directions of surgical instruments are labeled in the figures.

It is desirable to provide cannula identification systems and methods in which a cannula is automatically detected (e.g., determination of the presence of the cannula) and identified (e.g., determination of the type of the cannula). For instance, a surgical system may include a sensor that automatically detects identification information about the cannula when the cannula is used with the surgical system, such as when the cannula is attached to a component of the surgical system for use during a surgical procedure. The cannula may include a device that permits various numbers of unique combinations of identification information to be provided so the identification information includes information about various aspects of the cannula. The device may include the identification in a format that is automatically detected by a reader machine.

Various exemplary embodiments of the present disclosure contemplate identification devices, systems, and methods useful for identifying a cannula of a surgical system. The cannula may comprise a bowl portion forming a proximal end, a tube forming a distal end, and an attachment portion configured to be connected to an arm of a patient side cart to connect the cannula to the patient side cart. The cannula may include an identification device including identification information about the cannula in format that is automatically obtained, such as by a reader machine. According to one example, the identification device is located in the attachment portion. The identification device may comprise a magnet that represents the identification information via predetermined parameters of the magnet. The magnet may be a samarium cobalt magnet or other permanent magnet material familiar to one of ordinary skill in the art. The identification device may comprise a plurality of magnet positions and a magnet located in at least one of the magnet positions. The identification information may be represented by the presence or absence of a magnet in the magnet positions and a polarity of a magnetic field of the magnet. The identification information may comprise at least one of a length of the tube, a diameter of the tube, a material of the cannula, whether the tube is straight or includes a curved portion, and/or whether the cannula is configured for a surgical instrument with an end effector or for an imaging instrument.

Various exemplary embodiments of the present disclosure also contemplate a patient side cart of a surgical system that includes a reader to obtain identification information from an identification device of a cannula. The cart comprise a base, a main column, and an arm to which a cannula may be connected. The reader may be located in the cart. The reader includes, for example, at least one sensor configured to detect a magnet, such as, for example, a Hall effect device.

The reader may comprise at least one sensor group, with each sensor group comprises a plurality of sensors. In one example, each sensor group comprises an omnipolar polarity sensor to detect the polarity of a magnet in a corresponding magnet position of an identification device. In another example, the sensor groups each comprise a presence sensor to detect the presence of a magnet in a corresponding magnet position of an identification device and a polarity sensor to detect a selectively predetermined magnetic pole of the magnet. The sensor groups may each comprise a plurality of presence sensors and two polarity sensors, with one polarity sensor to detect a north polarity magnetic field and one polarity sensor to detect a south polarity magnetic field. The presence sensors may be omnipolar sensors and the polarity sensors may be unipolar sensors. In another example, a sensor comprises a magnetic field direction sensor configured to detect the angular orientation of a magnetic field of a magnet of an identification device.

Although the readers of the exemplary embodiments described herein may be described as being part of a surgical system, such as, for example, a manipulator arm of a patient side cart, the readers of the exemplary embodiments described herein may also be used as a manual device. For example, a reader is a hand-held device used by a user to quickly identify various cannulas without the use of a surgical system. For instance, a user may want to identify cannulas before or after a surgical procedure, such as to sort cannulas according to type.

Referring now to FIG. 1, an exemplary embodiment of a patient side cart 100 of a teleoperated surgical system is shown. A teleoperated surgical system may further include a surgeon console (not shown) for receiving input from a user to control instruments of patient side cart 100, as well as an auxiliary control/vision cart (not shown), as described in, for example, U.S. Pub. No. US 2013/0325033, entitled "Multi-Port Surgical Robotic System Architecture" and published on Dec. 5, 2013, and U.S. Pub. No. US 2013/0325031, entitled "Redundant Axis and Degree of Freedom for Hardware-Constrained Remote Center Robotic Manipulator" and published on Dec. 5, 2013, each of which is hereby incorporated by reference in its entirety. Non-limiting, exemplary embodiments of teleoperated surgical systems with which the principles of the present disclosure may be utilized include the da Vinci® Si (model no. IS3000) da Vinci® Si Surgical System, Single Site da Vinci® Surgical System, or a da Vinci® Xi Surgical System, available from Intuitive Surgical, Inc. of Sunnyvale, Calif.

Patient side cart 100 includes a base 102, a main column 104, and a main boom 106 connected to main column 104. Patient side cart 100 also includes a plurality of arms 110, 111, 112, 113, which are each connected to main boom 106. Arms 110, 111, 112, 113 each include an instrument mount portion 120 to which an instrument 130 may be mounted, which is illustrated as being attached to arm 110. Portions of arms 110, 111, 112, 113 may be manipulated during a surgical procedure according to commands provided by a user at the surgeon console. In an exemplary embodiment, signal(s) or input(s) transmitted from a surgeon console are transmitted to the control/vision cart, which may interpret the input(s) and generate command(s) or output(s) to be transmitted to the patient side cart 100 to cause manipulation of an instrument 130 (only one such instrument being mounted in FIG. 1) and/or portions of arm 110 to which the instrument 130 is coupled at the patient side cart 100.

Instrument mount portion 120 comprises an actuation interface assembly 122 and an accessory mount 124, with a shaft 132 of instrument 130 extending through accessory mount 124 (and on to a surgery site during a surgical procedure) and a force transmission mechanism 134 of instrument connecting with the actuation interface assembly 122, according to an exemplary embodiment. Accessory mount 124 is configured to hold a cannula (not shown in FIG. 1) through which shaft 132 of instrument 130 may extend to a surgery site during a surgical procedure. Actuation interface assembly 122 contains a variety of drive and other mechanisms that are controlled to respond to input commands at the surgeon console and transmit forces to the force transmission mechanism 134 to actuate instrument 130, as those skilled in the art are familiar with.

Although the exemplary embodiment of FIG. 1 shows an instrument 130 attached to only arm 110 for ease of viewing, an instrument may be attached to any and each of arms 110, 111, 112, 113. An instrument 130 may be a surgical instrument with an end effector or may be an endoscopic imaging instrument or other sensing instrument utilized during a surgical procedure to provide information, (e.g., visualization, electrophysiological activity, pressure, fluid flow, and/or other sensed data) of a remote surgical site. In the exemplary of FIG. 1, a surgical instrument with an end effector or an imaging instrument may be attached to and used with any of arms 110, 111, 112, 113. However, the embodiments described herein are not limited to the exemplary embodiment of FIG. 1 and various other teleoperated surgical system configurations may be used with the exemplary embodiments described herein.

Cannulas may have a variety of differing configurations that are useful to various types of surgical procedures. For example, cannulas may have varying lengths, diameters, materials, curvatures, and configurations based on which instrument types for which they are used, amongst other parameters. As a result, many differing cannula configurations are possible, particularly when considering the possible combinations of the various parameters of a cannula that may vary. In view of this consideration, it would be desirable to provide a system capable of automatically identifying different cannula types. For instance, it would be desirable to provide a teleoperated surgical system capable of automatically identifying different cannula types, such as when a cannula is installed on an arm of a patient side cart. Further, it would be desirable if an identification device of a cannula is durable and capable of withstanding repeated use, including cleaning procedures.

Figure 2:
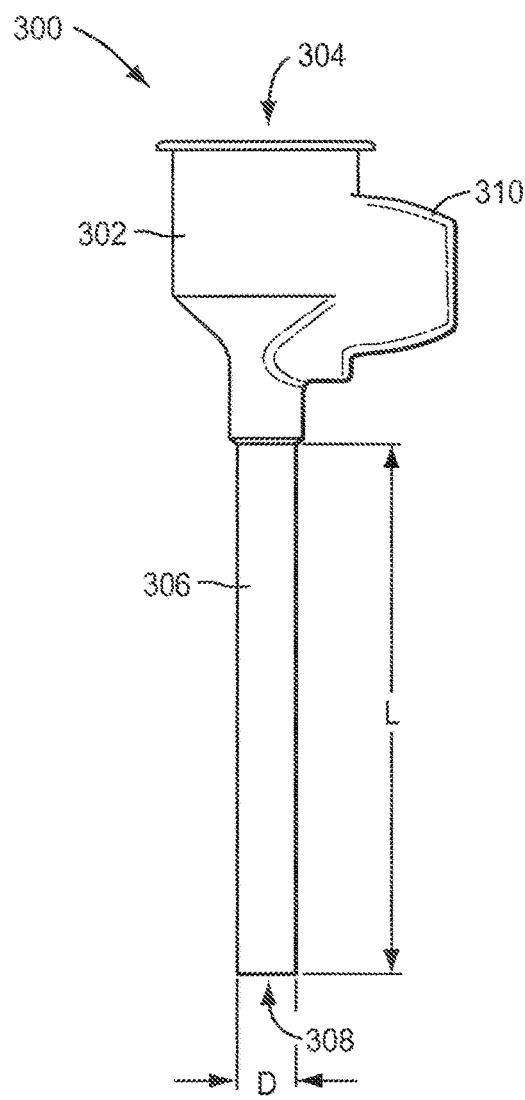
FIG. 2 is a side view of a cannula, according to an exemplary embodiment.
Figure 3:
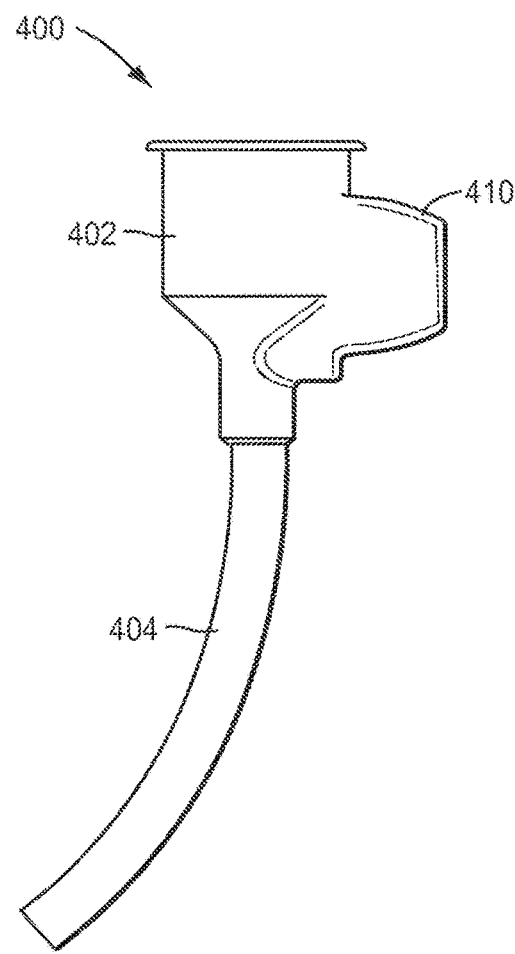
FIG. 3 is a side view of a cannula with a curved tube, according to an exemplary embodiment.

Turning to FIG. 2, a side view of an exemplary embodiment of a cannula 300 is shown. Cannula 300 may include an attachment portion 310, a bowl portion 302 forming a proximal end 304 of cannula 300, and a tube 306 extending from bowl portion 302 to a distal end 308 of cannula 300. The present disclosure contemplates bowl portions having a funnel configuration with a wide opening at one end (e.g., at proximal end 304) that leads to a smaller opening at an end (e.g., towards distal end 308) where the bowl portion is connected to a tube portion. The proximal and distal directions with respect to the orientation of FIG. 2 are labeled. As shown in the exemplary embodiment of FIG. 2, tube 306 may have a length L and distal end 308 may have a diameter D, each of which may vary depending on a desired application of cannula 300, as those having ordinary skill in the art are familiar with. Further, as shown in the exemplary embodiment of FIG. 2, tube 306 is straight, although the exemplary cannula embodiments described herein are not limited to a straight tube. For example, a cannula 400 includes an attachment portion 410, a bowl portion 402, and a curved tube 404 (e.g. a tube having a curved longitudinal axis along all or part of its length), as shown in the exemplary embodiment of FIG. 3.

Cannula 300 may be inserted through an opening in a patient's body to a surgical site. For example, distal end 308 of cannula may be inserted through an opening, such as, for example, an incision, natural orifice, or port, to a surgical site. A surgical instrument, such as instrument 160 in the exemplary embodiment of FIG. 1, can be inserted through cannula 300 to the surgical site. For example, an instrument may be inserted into proximal end 304 of cannula and extended through bowl section 302, tube 306, and distal end 308 of cannula 300 to a surgical site.

According to an exemplary embodiment, cannula 300 may be attached to an accessory mount to connect the cannula to an arm of a patient side cart, such as accessory mount 124 of an arm 110, 111, 112, or 113 of patient side cart 100 of the exemplary embodiment of FIG. 1. For example, cannula 300 includes an attachment portion 310 to connect cannula 300 to an accessory mount of an arm. Attachment portion 310 is, for example, a projection configured to be inserted into and held by an accessory mount of an arm, according to an exemplary embodiment. As shown in the exemplary embodiment of FIG. 2, attachment portion 310 is part of, or otherwise joined to, a bowl portion 302 of cannula 300.

Figure 4:
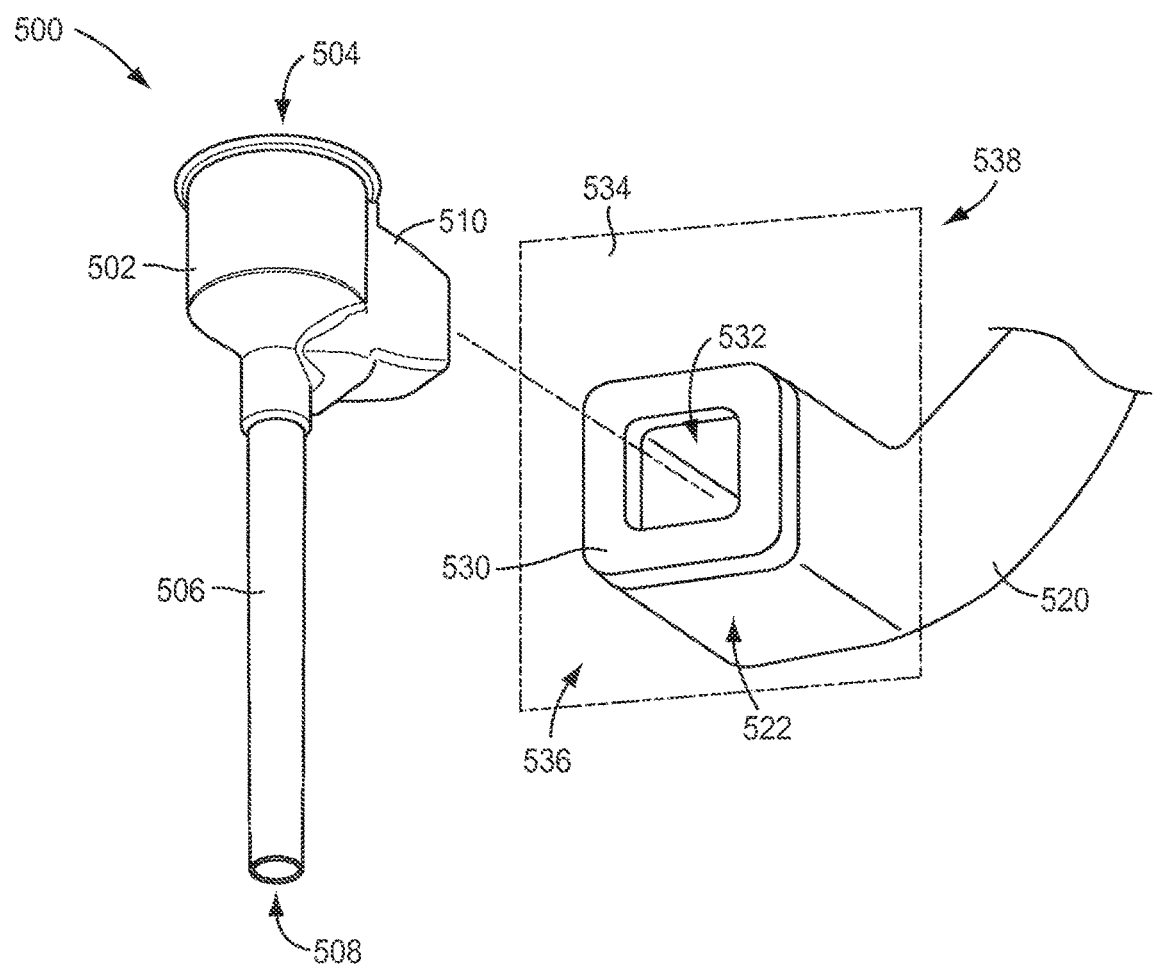
FIG. 4 is a perspective view of a cannula and arm to which the cannula is connected, according to an exemplary embodiment.

Turning to FIG. 4, an exemplary embodiment of a cannula 500 and a portion of an arm 520 of a patient side cart are shown in a disconnected state. Arm 520 is, for example, one of arms 110, 111, 112, 113 of patient side cart 100 of the exemplary embodiment of FIG. 1. Cannula 500 may be configured according to the various exemplary embodiments herein and may include, for example, an attachment portion 510, a bowl portion 502 forming a proximal end 504, and a tube portion 506 extending from bowl portion 502 to a distal end 508. Cannula 500 may be connected to arm 520 by inserting attachment portion 510 into an accessory mount 522 of arm 520, such as, for example, accessory mount 124 in the exemplary embodiment of FIG. 1.

According to an exemplary embodiment, accessory mount 522 of arm 520 includes a sterile adaptor 530. Sterile adaptor 530 may include a recess 532 into which attachment portion 510 of cannula 500 may be inserted for attachment of cannula 500 to arm 520. Sterile adaptor 530 may provide a boundary between a sterile region and non-sterile region. For instance, sterile adaptor 530 is located between cannula 500 and arm 520, thus maintaining a barrier between cannula 500, at least a portion of which is located in a sterile area during a surgical procedure, and arm 520, which may be in a non-sterile area during a surgical procedure. According to an exemplary embodiment, a surgical drape 534 (a portion of which is indicated schematically in FIG. 4 with dashed lines) is connected to sterile adaptor 530 to form a barrier between a sterile side 536, in which at least a portion of cannula 500 is located, and a non-sterile side 538, in which arm 520 is located.

Figure 5:
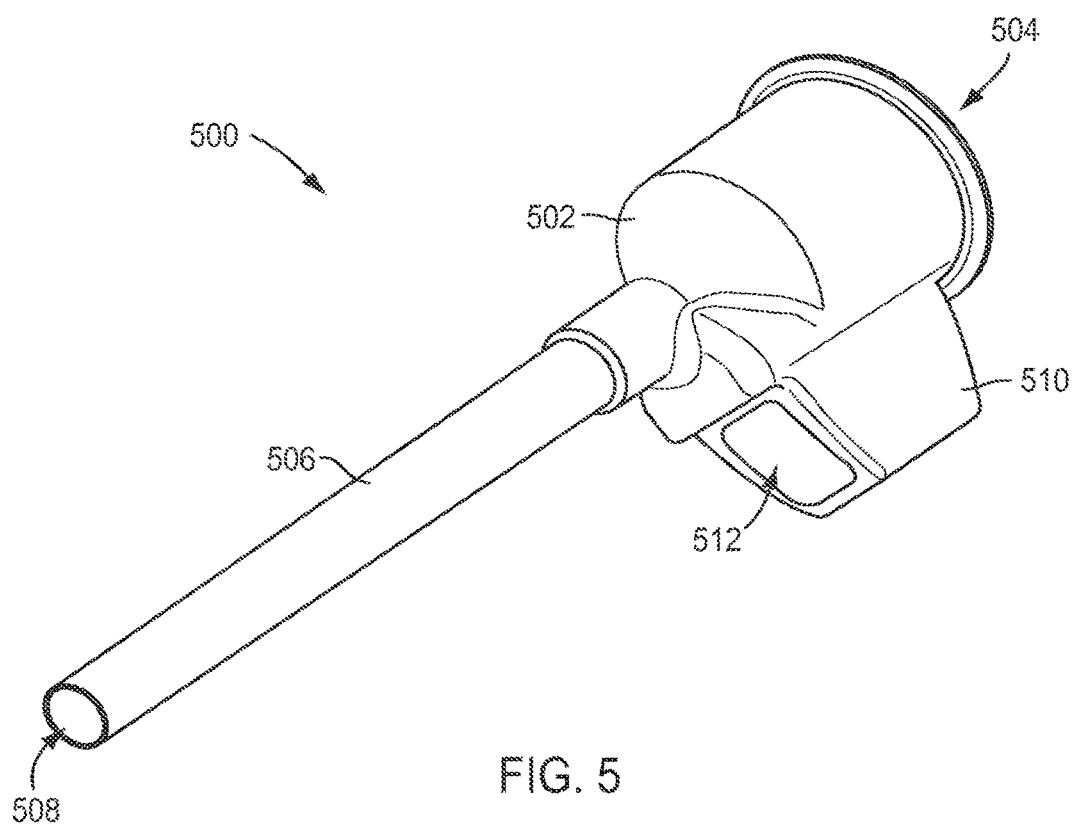
FIG. 5 is a bottom perspective view of a cannula including an identification device, according to an exemplary embodiment.

As discussed above, various parameters of a configuration of a cannula may be varied, permitting various possible combinations of the parameters of a cannula. Therefore, it may be desirable for a cannula to include an identification device so a cannula may be automatically identified by a surgical system, such as when a cannula is connected to a surgical system. The identification device includes information about the configuration of a cannula so the information to permit a machine reader to automatically obtain the information. For example, identification information may include information about a length, a diameter, a material of the cannula, whether the cannula tube is straight or curved, whether the cannula is for a surgical instrument with an end effector or for an imaging instrument, and/or other parameters. Turning to FIG. 5, a perspective view of cannula 500 of the exemplary embodiment of FIG. 4 is shown. According to an exemplary embodiment, cannula 500 includes an identification device in attachment portion 510 of cannula 500. For example, identification device is located in a distal portion 512 of attachment portion 510, although the exemplary embodiments in accordance with the present disclosure are not limited to the identification device being located in distal portion 512.

According to an exemplary embodiment, the identification device of a cannula interacts with a reader of a surgical system. For example, when an attachment portion of a cannula is attached to an arm of a surgical system, a reader located in arm interacts with the identification device in attachment portion and automatically obtains identification information about the cannula from the identification device. Thus, when attachment portion 510 of cannula 500 is attached to arm 520 in the exemplary embodiment of FIG. 4, such as via surgical adaptor 530, a reader located in arm may obtain identification information about cannula 500 from an identification device located in attachment portion 510.

Figure 6:
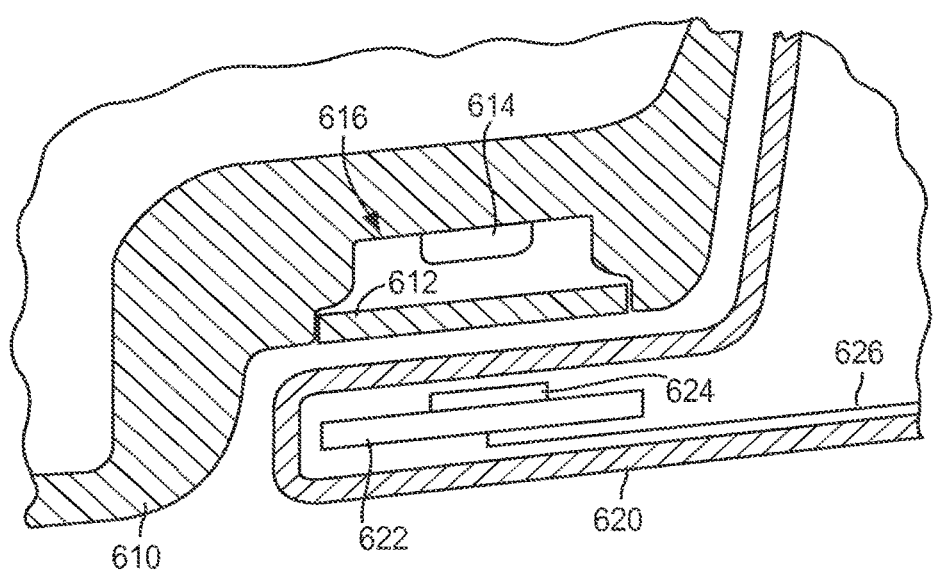
FIG. 6 is a partial side cross-sectional view of a cannula attachment portion connected to a patient side cart manipulator arm, according to an exemplary embodiment.

FIG. 6 depicts a partial cross-sectional view is shown of an attachment portion 610 attached to an arm 620 of a patient side cart. Attachment portion 610 and arm 620 may be arranged according to the exemplary embodiment of FIG. 4, such as attachment portion 510 of cannula 500 and arm 520. Thus, although a sterile adaptor is not shown for simplicity in the exemplary embodiment of FIG. 6, a sterile adaptor may be located between attachment portion 610 and arm 620, as discussed above with regard to sterile adaptor 530 and drape 534 of the exemplary embodiment of FIG. 4, without altering the principles of operation of the identification device and reader described below.

As shown in FIG. 6, attachment portion 610 may include an identification device 614 to provide identification information for a cannula. Arm 620 may include a reader 622 to receive identification information from identification device 614. According to an exemplary embodiment, reader 622 includes a sensor 624 to receive identification information from identification device 614. Although, reader 622 may include a single sensor, such as, for example, a single sensor 624 for identification device 614, the exemplary embodiments described herein are not limited to a single sensor for a reader. Rather, reader 622, according to exemplary embodiments, include one, two, three, four, five, six, seven, eight, nine, ten, eleven, twelve, thirteen, fourteen, fifteen, sixteen, or more sensors 624. For example, reader 622 includes a plurality of sensors in an array, as will be discussed below. Reader 622 may further include one or more transmission lines 626 to transmit signal(s) from reader 622 to a surgical system, such as to transmit a signal including identification information obtained from a cannula.

Figure 7:
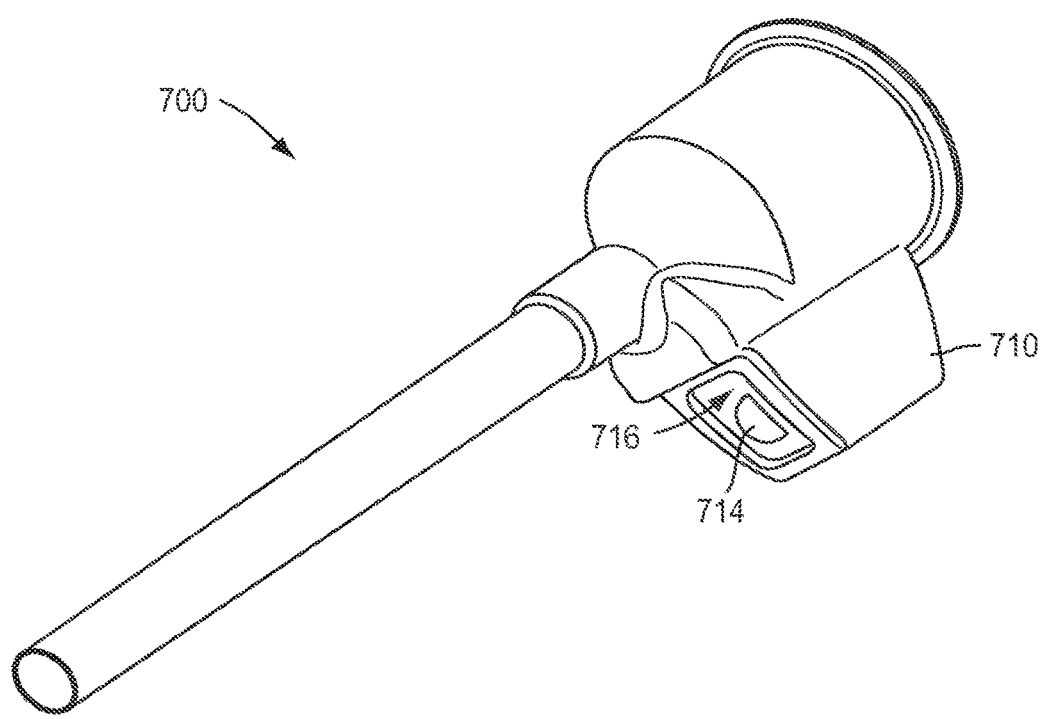
FIG. 7 is a bottom perspective view of a cannula with an identification device, according to another exemplary embodiment.
Figure 16:
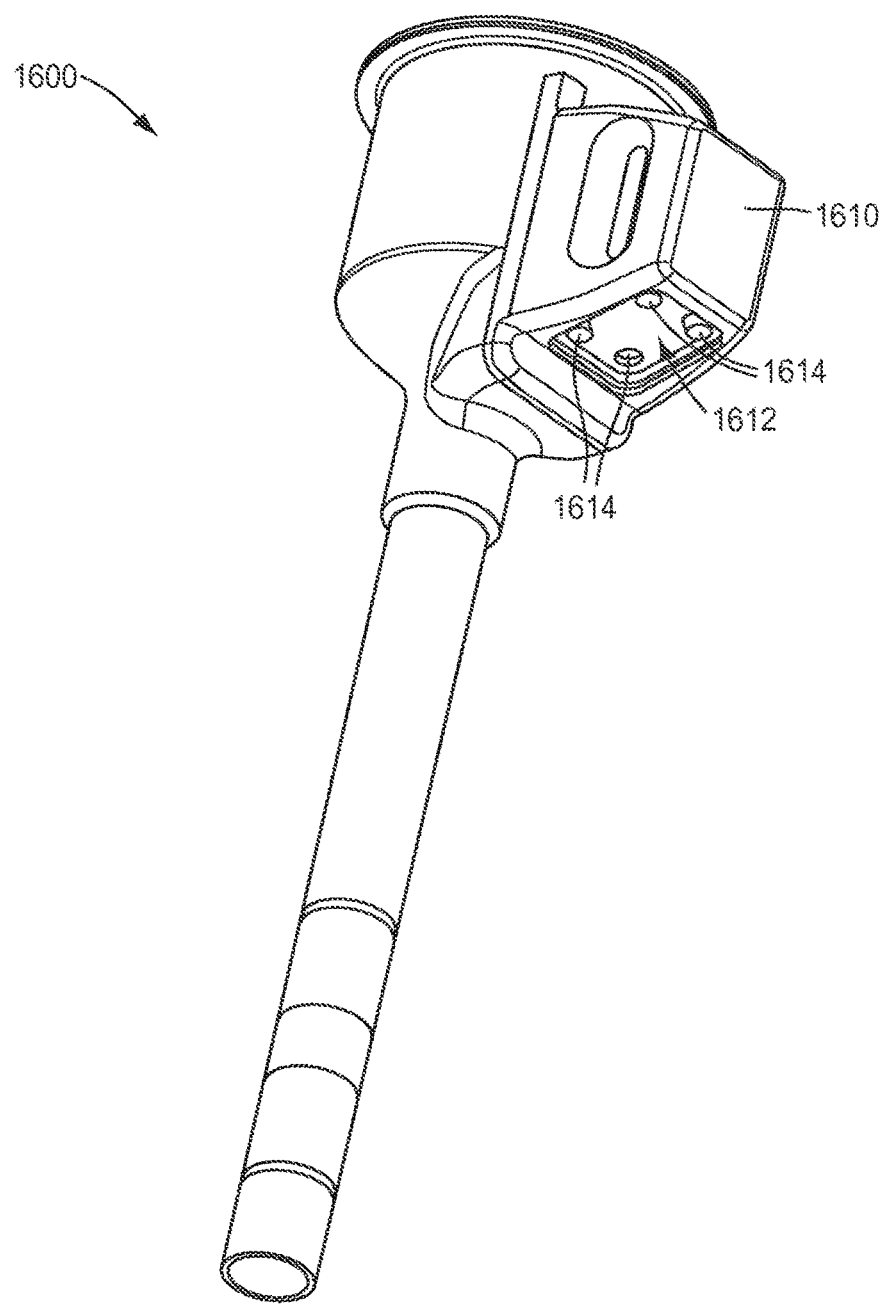
FIG. 16 is a bottom perspective view of a cannula including an array of plural magnet positions, according to an exemplary embodiment.

Identification devices in accordance with exemplary embodiments may provide identification information, such as in a format automatically read by a machine, in various ways. According to an exemplary embodiment, an identification device includes a magnet that is sensed by a reader, with the magnetic pole that is sensed by the reader serving as identification information. For instance, a magnet may be positioned in a cannula so a predetermined magnetic pole of the magnet faces a reader. According to an exemplary embodiment, an end of a magnet having a desired polarity (i.e., north or south polarity) may be positioned on a cannula to face toward a reader. As shown in the exemplary embodiment of FIG. 7, a cannula 700 includes a magnet 714 as an identification device 714. In FIG. 7, magnet 714 projects from a surface 716 of attachment portion 710 so a predetermined pole of the magnet 714 faces a reader, such as the reader 622 in the exemplary embodiment of FIG. 6, when attachment portion 710 is connected to an arm of a patient side cart. Although a single magnet 714 is shown projecting from surface 716 in the exemplary embodiment of FIG. 7, an identification device may include a plurality of magnets 714 projecting from surface 716. For example, a cannula 1600 may include an attachment portion 1610 having an array 1612 including a plurality of magnet positions 1614 for one or more magnets, as depicted in the exemplary embodiment of FIG. 16. Positioning identification device 714 so as to project from surface 716 may reduce interference between identification device 714 and cannula 700, such as when cannula 700 is made of a magnetic metal, such as, for example, 17-4 type stainless steel. According to an exemplary embodiment, identification device 714 is positioned so approximately half of identification device 714 is embedded within cannula 700 and approximately half of identification device 714 projects from surface 716. However, other positions of magnet of identification device are contemplated as being within the scope of the present disclosure.

In the exemplary embodiment of FIG. 7, identification device 714 is exposed. However, the exemplary embodiments described herein are not limited to an exposed identification device and may instead include an identification device that is not exposed. For example, an identification device 614 is covered, such as by a cover portion 612, as shown in the exemplary embodiment of FIG. 6. When identification device 614 is a magnet, cover portion 612 may be made of metal. According to an exemplary embodiment, cover portion 612 is made of a non-magnetic material, such as, for example, an austenitic stainless steel. Cover portion 612 may be joined to attachment portion 610 via, for example, welding, brazing, soldering, an adhesive, or other joining methods familiar to one of ordinary skill in the art. According to an exemplary embodiment, cover portion 612 is joined to attachment portion 610 so that cover portion 612 is sealed (e.g., has a liquid-tight seal) to attachment portion 610.

The type of magnet used in an identification device may be selected according to various parameters. According to an exemplary embodiment, in a cannula including an array of magnets and a reader including a reader configured to detect each magnet, a magnet may be selected to have a magnetic field strength sufficient to be detected by the particular reader configured and positioned with the purpose of detecting the magnet, but not too strong so as to be detected by another reader configured and positioned with the purpose of detecting a different magnet. Therefore, magnets of various exemplary embodiments described herein may have a magnetic field strength of, for example, about 17 gauss to about 19 gauss. According to an exemplary embodiment, magnets may be selected to withstand repeated uses in a cannula, including repeated sterilization processes. A sterilization process may include autoclaving, which may subject a magnet to elevated temperatures, which may even exceed the Curie temperature of a magnet. In view of this consideration, a magnet may be a permanent magnet made of a samarium-cobalt alloy, a neodymium alloy, or other permanent magnet materials familiar to one of ordinary skill in the art. An example of a permanent magnet is a samarium-cobalt grade 1-5 magnet sold by McMaster-Carr of Princeton, N.J.

As discussed above, a magnet may be used as an identification device to provide identification information for the cannula carrying the magnet. To provide a desired number of combinations of variables that correspond to the various parameters that may be included in identification information used to uniquely identify a particular cannula type (such as, for example, cannula length, diameter, material, whether the cannula is straight or curved, whether the cannula is for a surgical instrument with an end effector or for an imaging instrument, and other parameters), a plurality of magnets may be used in an identification device of the exemplary embodiments described herein. For example, an identification device may include an array of magnets that are detected by a reader. Thus, not only the magnetic polarity of a magnet used as an identification device may be selectively predetermined to represent an item of identification information, but a position of a particular magnet within the array may also be selectively predetermined so that a position of the magnet within the array also represents an item of information. When presented with an array of magnets, a reader may be configured to determine not only whether a magnet is present within a particular location of the array, but also what the polarity of the magnet is. Thus, a magnet's presence or absence at a particular position in an array of magnets and a polarity of the magnet may correlate to differing parameters representing identification information in a format that is detected by a reader. In this way, predetermined parameters of one or more magnets may represent identification information for a cannula. For instance, many combinations of presence, position, and polarity in the array can be can be achieved to provide multiple sets of unique identification information for differing types of cannulas.

According to an exemplary embodiment, the presence or absence of a magnet at a given magnet position and the polarity of the magnet at the given magnet position can be used for unique identification information of a cannula (e.g., cannula material, cannula length, etc.), with the presence or absence of the magnet and the magnet's polarity representing different values for the parameter of identification information. According to another exemplary embodiment, the various values for the presence or absence of a magnet and magnet polarity at the various magnet positions of an identification device may be varied to provide various unique identifiers for different cannulas corresponding to specific cannulas. For instance, instead of assigning a particular parameter of cannula identification information to a particular magnet position (e.g., varying a presence or absence at a particular location to signify whether, for example, a cannula is made of metal or plastic), the various values for the magnet presence or absence and polarity at the various magnet positions of an identification device may be varied to provide unique identifiers analogous to unique serial numbers corresponding to a particular type of cannulas. For example, a first unique combination of the presence/absence and polarity (when present) of magnets at various magnet positions corresponds to a first cannula type, a second unique combination of the presence/absence and polarity (when present) of magnets at various magnet positions corresponds to a second cannula type, and so on.

Figure 8:
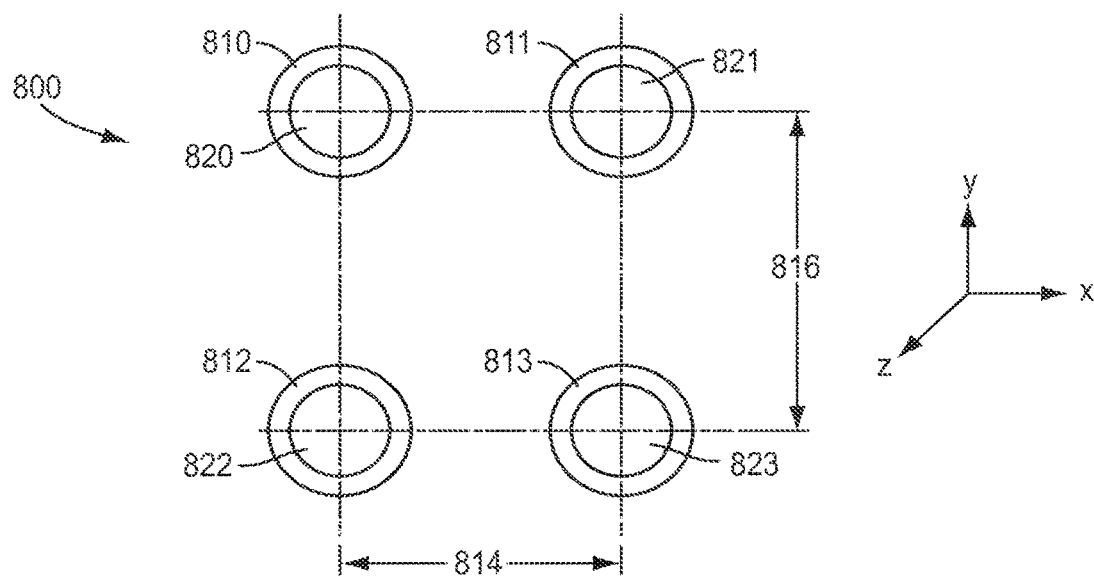
FIG. 8 is top schematic view of an identification device, according to an exemplary embodiment.

An array of magnets used in the identification devices of the exemplary embodiments described herein may have various numbers of magnets. Turning to FIG. 8, an exemplary embodiment of an array 800 of four magnet positions 810-813 is shown for an identification device, such as, for example, the identification devices 614, 714 of the exemplary embodiments of FIGS. 6 and 7. Although array 800 is depicted as including four magnet positions 810-813, array 800 may include other numbers of magnet positions, such as, for example, two, three, five, six, seven, eight, or more magnet positions. Magnet positions 810-813 represent positions where magnets may be located in array 800. In the exemplary embodiment of FIG. 8, array 800 includes a total number of four magnets 820-823 located at respective magnet positions 810-813. Array 800 is located in a cannula, such as in an attachment portion of a cannula, so that magnets 810-813 are detected by a reader to convey identification information, as discussed above with regard to FIG. 6.

According to an exemplary embodiment, each magnet position 810-813 indicates a particular parameter that provides a portion of identification information. Further, the presence or absence of a magnet at a particular magnet position may indicate a particular parameter providing identification information for a cannula. Although a total of four magnets 820-823 are shown in array 800 of the exemplary embodiment of FIG. 8, with a magnet 820-823 at each respective magnet position 810-813, the exemplary embodiments described herein are not limited to this embodiment. For example, various numbers of magnets may be located in an array including (n) number of magnet positions to use the presence or absence of a magnet at particular magnet position to indicate a parameter of identification information. For example, a total number of magnets of (n), (n−1), (n−2), (n−3), (n−4), (n−5), and so on may be used. According to an exemplary embodiment, an array of magnet positions includes at least one magnet.

In addition, a polarity of a magnet in each magnet position (when a magnet is present) may be predetermined to indicate a parameter of identification information. For example, magnets 820-823 respectively located in magnet positions 810-813 are each predetermined to have a polarity of north or south to be detected by a reader. According to an exemplary embodiment, when a reader detects the presence of north or south polarity for a particular magnet position, the reader also thereby detects the presence of a magnet at the particular magnet position.

By varying the presence or absence of a magnet and the polarity of a magnet at particular magnet positions in an array, numerous combinations of select parameters may be produced to provide overall identification information of a cannula. One magnet position, for example, may be used to signify how many magnets are present in an array of magnets so that a surgical system including a reader may determine whether the correct number of magnets has been detected. According to another example, the various combinations of magnet presence/absence and polarity are used to provide unique identifiers which are analogous to serial numbers for different cannula types. For example, in the arrangement of the exemplary embodiment of FIG. 8, there are 81 possible unique combinations when considering the four magnet positions 810-813 and three magnet states (e.g., a magnet present with a north polarity, a magnet present with a south polarity, or no magnet present). This number of possible unique combinations may be modified according to a desired design. For instance, it may be desirable to always have a magnet present so at least one magnet can be detected to determine the presence of cannula, which reduces the possible number of combinations by 1 since the combination of zero magnets being present has been eliminated.

By way of nonlimiting examples only, the following provides an explanation of possibilities for how the magnets of FIG. 8 can be used analogous to serial numbers to identify unique cannula types. In an exemplary embodiment, when magnet 821 is present at magnet position 811 and has a south polarity field and no magnet is located at any of magnet positions 810, 812, or 813, the array is assigned to correspond to a standard disposable cannula. A disposable cannula may be made of, for example, plastic or other disposable cannula material familiar to persons having ordinary skill in the art. For example, in one exemplary embodiment, the bowl portion 502, tube portion 506, and attachment portion 510 of cannula 500 in FIG. 5 are each made of a plastic material. According to an exemplary embodiment, a cannula made of plastic may include a single magnet to identify the cannula as a plastic cannula, such as a single magnet at position 811 (e.g., a magnet having a south polarity field). A magnet may be mounted to a plastic cannula via, for example, overmolding the magnet with the plastic material of the cannula, heat staking, adhesive, mounting a cover over the magnet, or other mounting methods familiar to persons having ordinary skill in the art.

In another example, when magnet 820 is present at magnet position 810 and has a south polarity field, magnet 821 is present at magnet position 811 and has a south polarity field, magnet 822 is present at magnet position 812 and has a south polarity field, and no magnet is present at magnet position 813, the array may be assigned to correspond to a standard non-disposable cannula. In another example, when magnet 820 is present at magnet position 810 and has a south polarity field, magnet 821 is present at magnet position 811 and has a north polarity field, magnet 822 is present at magnet position 812 and has a south polarity field, and no magnet is present at magnet position 813, the array is assigned to correspond to a non-disposable cannula with a long tube. In another example, when magnet 820 is present at magnet position 810 and has a south polarity field, no magnet is present at magnet position, magnet 822 is present at magnet position 812 and has a south polarity field, and magnet 823 is present at magnet position 813 and has a south polarity field, the array is assigned to correspond to a standard non-disposable cannula.

The preceding examples and additional examples are provided in Table 1 below, with the magnet locations corresponding to magnet locations 810-813 of the exemplary embodiment of FIG. 8. Table 1 includes examples of sensor signals from an exemplary embodiment of a reader that includes sensor to detect the presence/absence and polarity of a magnet at each magnet. Thus, a "N" in Table 1 indicates the presence of a magnet with a north polarity and an "S" in Table 1 indicates the presence of a magnet with a south polarity. An "--" indicates that no magnet is present.

TABLE 1

| Magnet Location 810 | Magnet Location 811 | Magnet Location 812 | Magnet Location 813 | Corresponding Cannula |
|---|---|---|---|---|
| — | S | — | — | Standard disposable cannula |
| — | — | N | — | Long disposable cannula |
| S | S | S | — | Standard non-disposable cannula |
| S | N | S | — | Long non-disposable cannula |
| S | S | — | S | Camera cannula |

The configurations of magnets in an array may be selected to minimize or eliminate interference. According to an exemplary embodiment, the page of FIG. 8 represents surfaces 616 and 716 in the exemplary embodiments of FIGS. 6 and 7, and ends of magnets 820-823 are configured to extend out of the page of FIG. 8, such as along axis Z in FIG. 8. Extending the ends of magnets 820-823 from a surface of a cannula may reduce interference with the magnetic field of magnets 820-823, such as, for example, interference caused by the material of a cannula. To minimize or eliminate interference between magnets 810-813, distances 814 and 816 along respective axes X and Y also may be controlled, such as during manufacture of a cannula. For example, in an exemplary embodiment in which no magnet is located at magnet position 810 but magnets 821 and 822 are respectively located at magnet positions 811 and 812, magnet 821 at position 811 is spaced a distance 814 along axis X from position 810 and magnet 822 at position 812 may be spaced a distance 816 along axis Y from position 810 to minimize a false positive detection of a magnet at position 810 due to the magnetic fields of magnets 821 and 822. According to an exemplary embodiment, distances 814 and 816 are, for example, distances between respective centers of magnet positions. Distance 814 ranges from, for example, about 0.310 inches to about 0.330 inches and distance 816 ranges from, for example, about 0.370 inches to about 0.390 inches, according to an exemplary embodiment.

Figure 9:
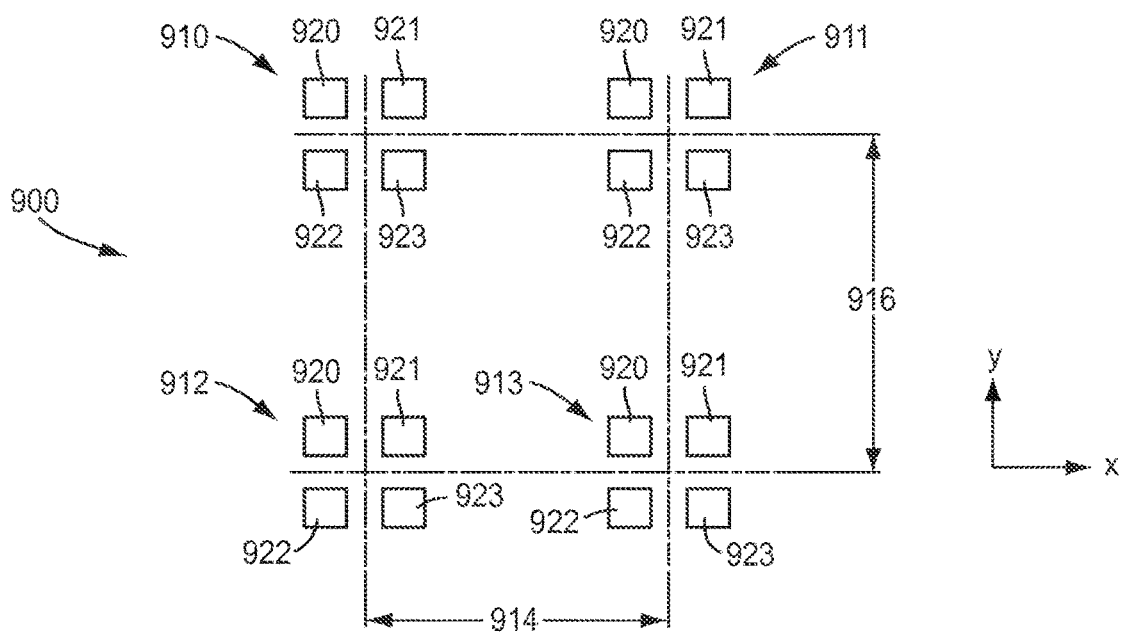
FIG. 9 is a top schematic view of a reader for use with an identification device, according to an exemplary embodiment.

Turning to FIG. 9, an exemplary embodiment of a reader 900 is shown schematically. Reader 900 may be used in the exemplary embodiments described herein, such as reader 622 of the exemplary embodiment of FIG. 6 for a surgical system, to obtain identification information from an identification device. Reader 900 may be configured so the reader is able to detect the components of an identification device to obtain identification information. For instance, if an identification device comprises an array of components with identification information, such as magnets 820-823 located at positions 810-813 in the exemplary embodiment of FIG. 8, reader 900 is configured to detect the components and obtain identification information from the components.

Reader 900 may comprise one or more sensors to detect the components of an identification device. As discussed above with regard to the exemplary embodiment of FIG. 6, reader 900 includes a single sensor to provide the functions of the sensors described in the exemplary embodiments discussed herein. In another exemplary embodiment, reader 900 includes a plurality of sensors to providing the sensing functions described in the exemplary embodiments discussed herein. For example, reader 900 includes a plurality of sensors, with respective sensors being configured to detect a respective component of an identification device.

According to an exemplary embodiment, reader 900 is configured to detect magnets 820-823 located at positions 810-813 of the identification device of the exemplary embodiment of FIG. 8, with reader 900 including sensor groups 910-913 respectively configured to detect magnets 820-823. For instance, when a cannula including identification device 800 is connected to an arm of a surgical system, as discussed above with regard to the exemplary embodiments of FIGS. 4 and 6, magnets 820-823 are positioned opposite and substantially in alignment with sensor groups 910-913 of reader 900 so sensor groups 910-913 respectively detect magnets 820-823 and separately obtain identification information from magnets 820-823, including from the absence of such magnets at a position 810-813. Thus, reader 900 may comprise four sensor groups 910-913 corresponding to the four magnet positions 810-813 of identification device 800 in the exemplary embodiment of FIG. 8. However, readers of the exemplary embodiments described herein are not limited to four sensor groups and may include other numbers of sensor groups according to the number of components of an identification device, such as the number of magnets. For example, a reader includes two, three, five, six, seven, eight, or more sensor groups. According to an exemplary embodiment, distance 914 along axis X and distance 916 along axis Y between sensor groups in the exemplary embodiment of FIG. 9 respectively correspond to distances 814 and 816 in the exemplary embodiment of FIG. 8.

Figure 10:
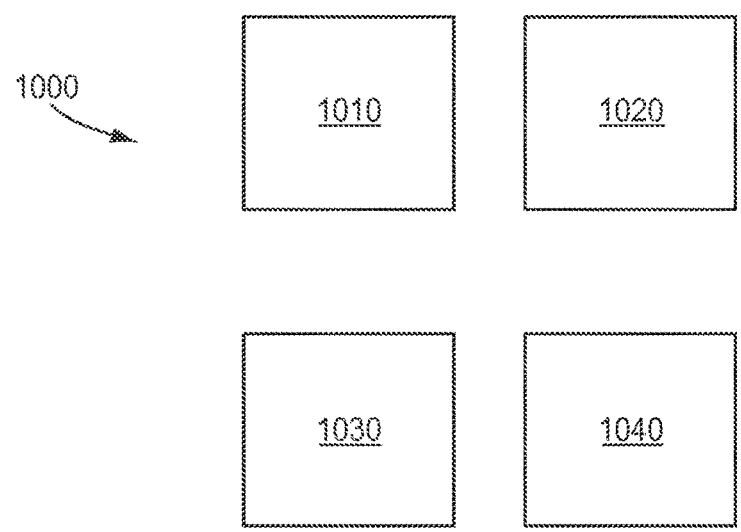
FIG. 10 is a top schematic view of a sensor group including four sensors, according to an exemplary embodiment.

A reader may comprise one or more sensors in each sensor group of the reader. Although a sensor group of the various exemplary embodiments described herein may include a single sensor (include a single sensor to accomplish the various sensor functions described herein), each sensor group may instead include a plurality of sensors. As shown in the exemplary embodiment of FIG. 9, each sensor group 910-913 may include four sensors 920-923, although the exemplary embodiments described herein are not limited to readers comprising sensor groups with four sensors each. Instead, each sensor group may comprise, for example, one, two, three, four, or more sensors. Turning to FIG. 10, an exemplary embodiment of a sensor group 1000 is shown schematically, with sensor group 1000 comprising four sensors 1010-1040. Sensor group 1000 and sensors 1010-1040 is used, for example, in each sensor group 910-913 of the exemplary embodiment of FIG. 9.

Because various types of identification information may be obtained from the components of an identification device, a sensor group may include a plurality of sensors to perform various functions to obtain the different types of identification information. For instance, in the exemplary embodiment of FIG. 8, the presence or absence of magnets 820-823 at magnet positions 810-813 could serve as one parameter of identification information and the selectively predetermined polarity of magnets 820-823 that are present at a position 810-813 may serve as another parameter of identification information to be obtained by a reader.

In accordance with this, sensors of a sensor group may be configured to detect whether a magnet is present at a magnet position and other sensors of a sensor group may be configured to detect the polarity of the magnet present. For example, sensor 1010 in the exemplary embodiment of FIG. 10 is a presence sensor configured to detect whether a magnet is present at a magnet position. In case sensor 1010 malfunctions or otherwise fails, sensor 1040 is also a presence sensor configured to detect the presence of a magnet to provide redundancy for the ability of sensor group 1000 to detect the presence of a magnet, according to an exemplary embodiment. To detect the polarity of a magnet, sensor 1020 may be configured to detect a north polarity field, while sensor 1030 may be configured to detect a south polarity field, or vice versa, according to an exemplary embodiment. Although sensors 1010, 1020, 1030, 1040 of sensor group 1000 have been described above as having specific functions, sensors 1010, 1020, 1030, 1040 can have different functions. For example, sensors 1010 and 1040 are polarity sensors and sensors 1020 and 1030 are presence sensors.

One type of sensor that may be used in a reader to detect a magnet is a Hall effect device, with those having ordinary skill in the art are familiar. A Hall effect device may be, for example, a Hall effect sensor, which may be configured to detect not only the presence of a magnet but a polarity of a magnetic field. A Hall effect sensor may include, for example, charge carriers (i.e., electrons and holes) flowing through a semiconductor (or conductor) that are deflected by the presence of a magnetic field, with the deflection resulting in a potential difference that may be detected. Although various exemplary embodiments are described herein as using Hall effect sensors, the embodiments may use other Hall effect devices and magnet sensors, such as, for example, a reed sensor or a Hall effect switch configured to merely detect the presence of a magnet, and other sensors familiar to one of ordinary skill in the art.

Figure 11:
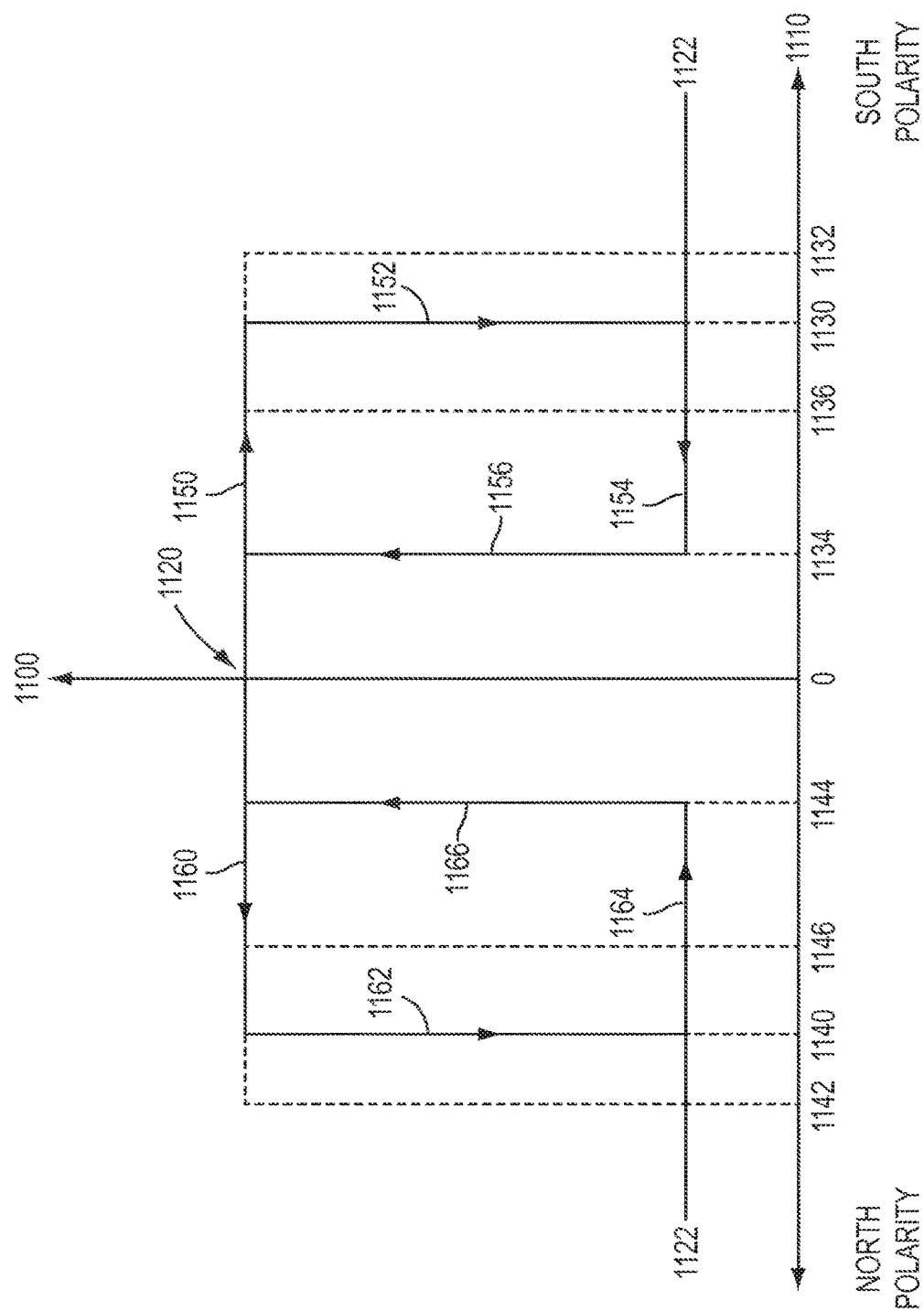
FIG. 11 is a schematic graph of voltage versus magnetic flux for a Hall effect device, according to an exemplary embodiment.

According to an exemplary embodiment, Hall effect devices used in a reader, such as for sensors 1010, 1020, 1030, 1040 and sensors 920-923 in the exemplary embodiments of FIGS. 9 and 10, can have a default high voltage state and a low voltage state when a magnet is proximate to the sensor. Turning to FIG. 11, an exemplary embodiment of the output voltage (indicated by axis labeled 1100) of a Hall effect device and a magnetic flux density (indicated by axis labeled 1110) are schematically shown.

With reference to FIG. 11, when a magnet is not in the presence of the Hall effect device, the magnetic flux density 1110 is 0 and the Hall effect device has a default voltage of 1120 (i.e., a "high" voltage state). As a magnet with a south polarity pole is brought proximate to the Hall effect device, the output voltage remains high as the magnet flux density 1110 increases along path 1150 until the minimum operating point 1130 for a south polarity magnetic pole has been reached. Once the minimum operating point 1130 has been reached, the Hall effect device may switch state to voltage 1122 (i.e., a "low" voltage state). In FIG. 11, a south polarity field is associated with flux on the right, while a north polarity field is associated with flux on the left, with magnetic flux increasing to the right and left of 0 flux for each polarity. A similar process occurs for a north polarity pole being brought proximate to the sensor, with the voltage level remaining high as magnetic flux 1110 increases along path 1160 until the flux falls between the minimum operating point 1140 and the maximum operating point 1142 for a north polarity pole, at which point the sensor switches to voltage 1122, such as along path 1162. Although the exemplary embodiment of FIG. 11 shows the Hall effect device switching to voltage 1122 at the minimum operating point 1130 along path 1152 and at the minimum operating point 1140 along path 1162, the Hall effect device may switch to voltage 1122 at any magnetic flux value within a magnetic flux release band defined between the respective minimum and maximum operating points 1130, 1132 and 1140, 1142.

As the distance between the Hall effect device and the magnetic pole increases, magnetic flux 1110 decreases, such as by removing the magnetic pole from proximity to the Hall effect device, such as toward 0 magnetic flux along path 1154 for a south polarity field or along path 1164 for a north polarity field. Once the magnetic flux 1110 has decreased to a value falling within a release point band, such as between maximum release point 1136 and minimum release point 1134 for a south polarity field or between maximum release point 1146 and minimum release point 1144 for a north polarity field, the Hall effect device reverts to its default voltage 1120 (the "high" voltage state), which indicates that a magnetic field is not present. Although the exemplary embodiment of FIG. 11 shows the Hall effect sensor switching to voltage 1120 at the minimum release point 1134 along path 1156 and at minimum release point 1166 along path 1166, the Hall effect device may switch to voltage 1120 at any magnetic flux value within a magnetic flux release band defined between the respective minimum and maximum release points 1134, 1136 and 1144, 1146.

The exemplary embodiment of FIG. 11 may apply to a magnet presence sensor, such as sensors 1010 and 1040 of the exemplary embodiment of FIG. 10, and to a magnet polarity sensor, such as sensors 1020 and 1030 of the exemplary embodiment of FIG. 10, although these different types of sensors may exhibit different release point values, operating point values, and/or voltage values, which will be discussed below, but otherwise will operate in the general manner discussed in regard to the exemplary embodiment of FIG. 11. For instance, when the Hall effect device has voltage 1122, the Hall effect device is indicating the presence of magnet, such as when a sensor is one of sensors 1010 and 1040 of the exemplary embodiment of FIG. 10. When the Hall effect device is configured to detect a magnetic polarity (e.g., by using a Hall effect sensor), such as devices 1020 and 1030 of the exemplary embodiment of FIG. 10, the voltage 1122 may be used to indicate the polarity of the magnetic pole being sensed.

According to an exemplary embodiment, a Hall effect device used to detect the presence of a magnet, such as sensors 1010 and 1040 of the exemplary embodiment of FIG. 10, is an omnipolar sensor that detects the presence of either a north polarity magnetic pole or a south polarity magnetic pole. Thus, an omnipolar presence sensor may follow either path 1150 or 1160 when a south polarity or north polarity pole is brought proximate to the sensor. In contrast, a sensor to detect the polarity of a magnetic pole may be a unipolar sensor configured to detect only one type of magnetic polarity, according to an exemplary embodiment. As discussed above with regard to the exemplary embodiment of FIG. 10, sensor 1020 may be configured to detect a north polarity field (and not a south polarity field), and thus follow path 1160 when a north polarity magnet is brought proximate to sensor 1020, while sensor 1030 may be configured to detect a south polarity field (but not a north polarity field) and follow path 1150 when a south polarity magnet is brought proximate to sensor 1030. A unipolar sensor will not respond to a magnetic field having a polarity it is not designed to detect.

A release point value for a sensor may be selected to minimize or prevent interference from magnetic fields not originating from a magnet to be detected by a sensor. According to an exemplary embodiment, a presence sensor has minimum release points 1134, 1144 that have higher values than the minimum release points 1134, 1144 for a polarity sensor. In this way, although the detection of a magnetic field by a polarity sensor could inherently indicate the presence of a magnet, the presence sensor is less sensitive to magnetic fields from sources other than a magnet proximate to the presence sensor, such as other magnets in an array of an identification device. Because polarity sensors may have lower release point values than presence sensors, a controller receiving signals from a reader may be configured to ignore a detection signal from a polarity sensor unless a presence sensor (or all presence sensors in the case of redundant presence sensors being used, as with sensors 1010 and 1040 in the exemplary embodiment of FIG. 10) also indicates the detection of a magnetic field, according to an exemplary embodiment. Thus, a presence sensor may be used to verify the presence of a magnet that has been detected by a polarity sensor, with the detection of a sensor by a polarity sensor being ignored unless at least one presence sensor in the same array also detects the magnet. According to an exemplary embodiment, polarity sensors of the exemplary embodiments discussed herein have values for minimum release points 1134, 1144 of, for example, ranging from about 7 gauss to about 9 gauss. Presence sensors of the exemplary embodiments discussed herein have values for minimum release points 1134, 1144 of, for example, ranging from about 11 gauss to about 13 gauss.

According to an exemplary embodiment, the presence sensors and polarity sensors of the exemplary embodiments discussed herein have maximum operating points 1132, 1142 of, for example, ranging from about 50 gauss to about 60 gauss, although the presence sensors and the polarity sensors may have different values for operating points 1130, 1132, 1140, 1142. An example of a presence sensor is model AH1892 from Diodes® Inc. of Plano, Tex. Examples of unipolar sensors are models BU52002GUL and BU52003GUL of Rohm Co., Ltd. of Kyoto, Japan.

Detection signals from sensors may be transmitted to a controller, such as via transmission lines 626 in the exemplary embodiment of FIG. 6, and interpreted by the controller, such as a controller of a surgical system. The surgical system may interpret the signals from various sensors of a reader to determine what identification information has been obtained and then identify what type of cannula is represented by the identification information. Signals from the sensors may also be analyzed for errors with the sensors. According to an exemplary embodiment, signals from the sensors of a reader also are analyzed to determine if a sensor is providing a false signal or if a sensor has malfunctioned. For instance, a reader includes a plurality of presence sensors to provide redundancy in a reader's presence detection capability so if one presence sensor fails another presence sensor detects a component of an identification device. Further, if unipolar polarity sensors are used to detect either a north or south polarity field, a controller may determine that one of the unipolar polarity sensors is malfunctioning when both unipolar sensors indicate the presence of a magnetic field. Conversely, if the presence sensor(s) of a reader indicate the presence of a magnet but no polarity sensor indicates the polarity of the field from the magnet, this indicates at least one of the unipolar polarity sensors is malfunctioning.

The following table provides examples of sensor signals from an exemplary embodiment of a reader that includes four sensors, with two sensors being omnipolar Hall effect presence devices ("P/A" in Table 2), such as devices 1010 and 1040 in the exemplary embodiment of FIG. 10, one sensor being a unipolar Hall effect polarity sensor to detect a north polarity field ("North" in Table 2), such as device 1020 in the exemplary embodiment of FIG. 10, and one sensor being a unipolar Hall effect sensor to detect a south polarity field ("South" in Table 2), such as device 1020 in the exemplary embodiment of FIG. 10. A value of "1" indicates a high state (e.g., voltage 1120 in FIG. 11), which is the default state indicating no detection, and a value "0" indicates a low state (e.g., voltage 1122 in FIG. 11), which is the detection state. An "X" indicates that a value of "1" or "0" could be present but either value would not affect the outcome of the result.

TABLE 2

| P/A | P/A | North Sensor | South Sensor | Result |
|---|---|---|---|---|
| 1 | 1 | X | X | No magnet present |
| 0 | 0 | 1 | 0 | Magnet present with south pole |
| 0 | 0 | 0 | 1 | Magnet present with north pole |
| 1 | 0 | X | X | Error: bad presence sensor |
| 0 | 1 | X | X | Error: bad presence sensor |
| 0 | 0 | 1 | 1 | Error: bad polarity sensor |
| 0 | 0 | 0 | 0 | Error: bad polarity sensor |

According to an exemplary embodiment, feedback is provided to a user, such as by displaying the identity of the cannula to the user. According to an exemplary embodiment, a controller is programmed to expect a cannula having a particular identification for a surgical procedure and if the identification information determined from the sensor signals does not match the programmed identification information, feedback can be provided to a user, such as via visual and/or audio feedback to notify the user of the mismatched identification information. According to an exemplary embodiment, the surgical system prevents use of a patient side cart, including arms and instruments connected to the arms of the patient side cart, when the determined identification information does not matched a programmed identification information.

Other uses of identification information for a cannula are encompassed by the various exemplary embodiments described herein, including but not limited to, for example, verifying that a cannula is made of metal (e.g., such as when an electrosurgical instrument will be used with a cannula), verifying that a cannula matches the type of cannula to be used with a particular instrument, informing a surgical system of the length of a cannula (e.g., informing a surgical system of cannula tube length), informing a surgical system that a cannula is present so safety features (e.g., patient side cart stabilizing features and features to immobilize a patient side cart) may be engaged, and other features related to cannula use with a surgical system.

Figure 12:
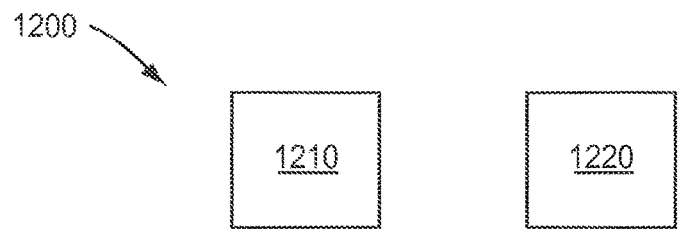
FIG. 12 is a top schematic view of a sensor group including three sensors, according to an exemplary embodiment.
Figure 13:
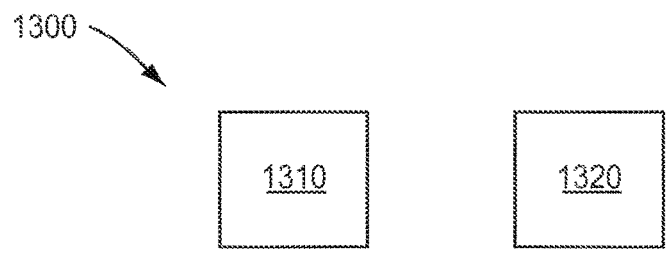
FIG. 13 is a top schematic view of a sensor group including two sensors, according to an exemplary embodiment.
Figure 14:
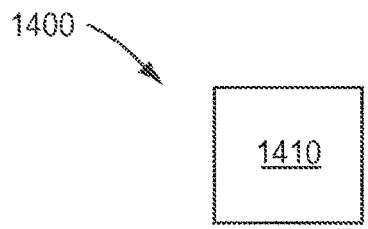
FIG. 14 is a top schematic view of a sensor group including one sensor, according to an exemplary embodiment.

Although the exemplary embodiments of FIGS. 8-10 have been discussed with regard to readers including sensor groups including four sensors each (such as sensors 920-923 in FIG. 9 and sensors 1010, 1020, 1030, 1040 in FIG. 10), sensor groups of a reader may include other numbers of sensors. Turning to FIGS. 12-14, various sensor groups 1200, 1300, 1400 are shown that may be used with the readers of the exemplary embodiments discussed above.

In FIG. 12, an exemplary embodiment of a sensor group 1200 is shown that includes three sensors 1210, 1220, and 1230. According to an exemplary embodiment, two of sensors 1210, 1220, and 1230 are unipolar polarity sensors and one of sensors 1210, 1220, and 1230 is an omnipolar presence sensor, as discussed above with regard to the exemplary embodiment of FIG. 11. According to another exemplary embodiment, two of sensors 1210, 1220, and 1230 are omnipolar presence sensors to provide presence sensing redundancy and one of sensors 1210, 1220, and 1230 is a dual output unipolar polarity sensor that detects both north and south polarity fields. According to an exemplary embodiment, although the dual output unipolar polarity sensor is capable of detecting both north and south polarity fields due to its dual outputs, the minimum release point 1134, 1144 for the dual output unipolar polarity sensor has a lower value than the minimum release point 1134, 1144 for the unipolar polarity sensor, making the dual output unipolar polarity sensor more sensitive to stray magnetic fields than the unipolar polarity sensor that does not have dual outputs. An example of a dual output unipolar sensor is model A1171 from Allegro® Microsystems, Inc. of Worcester, Mass.

In FIG. 13, an exemplary embodiment of a sensor group 1300 is shown that includes two sensors 1310 and 1320. One of sensors 1310 and 1320 may be an omnipolar presence sensor, as discussed above with regard to the exemplary embodiment of FIG. 11, and the other of sensors 1310 and 1320 may be a dual output unipolar polarity sensor that is capable of detecting both north polarity fields and south polarity fields, as discussed above with regard to the exemplary embodiment of FIG. 13. In FIG. 14, an exemplary embodiment of a sensor group 1400 is shown that includes a single sensor 1410 that is a dual output unipolar polarity sensor. A single sensor 1410 could be used by interpreting the detection of a north or south polarity field as indicating the presence of a magnet, without any corroboration from a presence sensor.

Figure 15:
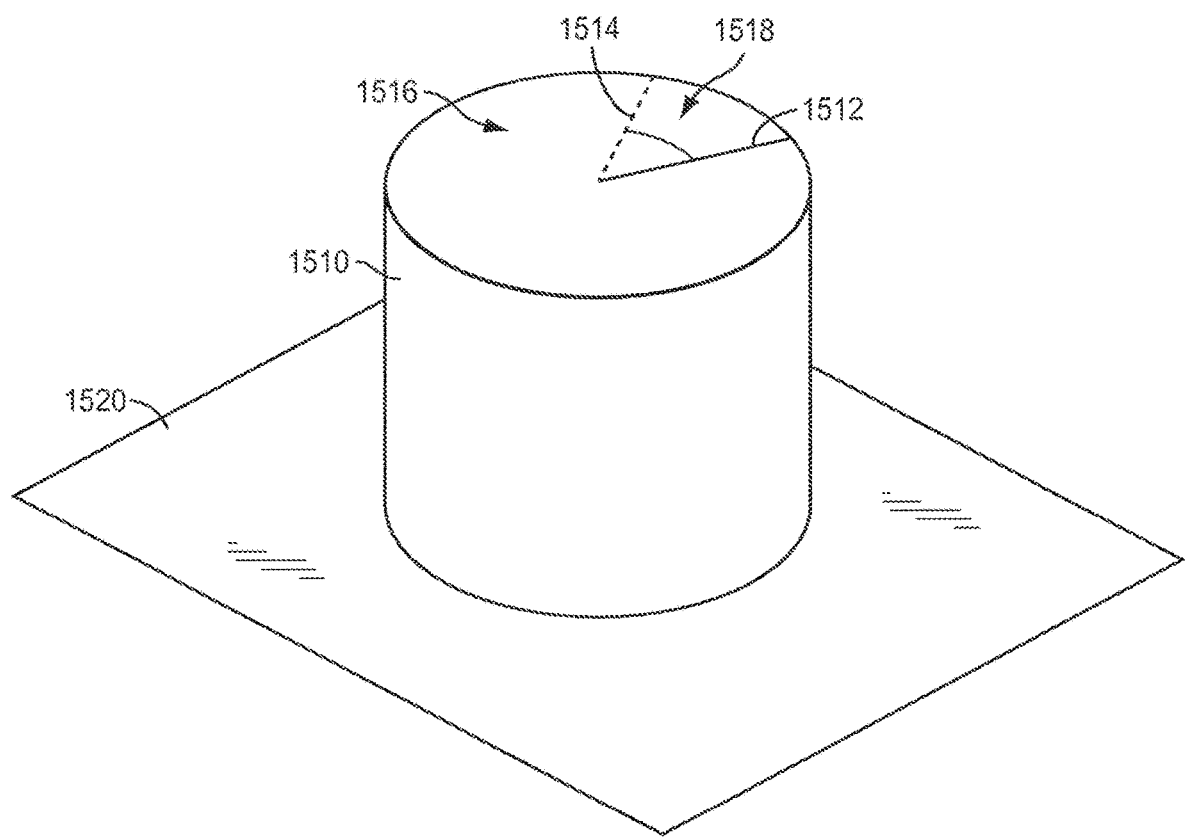
FIG. 15 is a perspective view of an identification device including an oriented magnet, according to an exemplary embodiment.

Although identification and reader embodiments have been discussed above with regard to the use of magnets and sensors to detect magnets, other types of identification devices and sensors may be utilized with the exemplary embodiments described herein. According to an exemplary embodiment, an identification device includes a magnet with a predetermined orientation representing identification information, which is detected by a reader. Turning to FIG. 15, an exemplary embodiment is shown of a magnet 1510 projecting from a surface 1520, which may be cannula surface 616 or 716 in the exemplary embodiments of FIGS. 6 and 7. Magnet 1510 may be a cylindrical magnet that has been selectively oriented so that the magnetic field of magnet 1510 is directed along a predetermined direction. According to an exemplary embodiment, magnet 1510 is oriented so that the magnet field of a pole at the end 1516 of magnet is directed along a direction 1512 oriented relative to a predetermined reference direction 1514. A reader may include a sensor to detect the angle 1518 between directions 1514 and 1516, with the identification angle conveying identification information to the reader. For instance, a sensor detects the magnetic field direction of a magnet of an identification device. According to an exemplary embodiment, the sensor is capable of detecting angle 1518 for magnetic field direction. The magnetic field direction sensor may be, for example, a magnetic rotary sensor including one or more linear Hall effect devices to detect the strength of a magnetic field along a particular direction, which is then analyzed to determine the angle of a magnetic pole to the magnetic field direction sensor. According to an exemplary embodiment, the magnetic field direction sensor uses mapped sensor angle values to correct for deviations in a field direction, such as due to the magnet fields of other magnets and/or other nearby magnetic materials.

Another type of identification device that may be used with the exemplary embodiments described herein is a radio frequency identification (RFID) device. According to an exemplary embodiment, a RFID device includes a device located in a cannula, with the device including electronically stored identification information that is obtained by a reader. The reader, for example, may emit an electromagnetic field that activates the device in the cannula, which in turn emits the identification information to be detected by the reader.

Although the exemplary embodiments herein have been described for identifying cannulas, the exemplary embodiments are used for the identification of other objects than a cannula. For example, the exemplary embodiments described herein are used to identify other surgical devices and non-surgical devices, such as, for example, devices that may be matched to a corresponding system that uses the device.

Although the readers of the exemplary embodiments described herein may be described as being part of a surgical system, such as, for example, a manipulator arm of a patient side cart, the readers of the exemplary embodiments described herein may also be used as a manual device. For example, a reader may be a hand-held device used by a user to quickly identify various cannulas without the use of a surgical system.

By providing a cannula for surgical system with an identification device, a cannula is accurately identified, including various unique features of a particular cannula. The identification device identifies a cannula without the use of electronic parts on a cannula, making the identification device low in complexity and cost. Further, the identification device is durable and capable of use over the lifetime of a cannula, even when the cannula is cleaned, such as via autoclaving.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present disclosure and following claims.

It is to be understood that the particular examples and embodiments set forth herein are non-limiting, and modifications to structure, dimensions, materials, and methodologies may be made without departing from the scope of the present disclosure.

Other embodiments in accordance with the present disclosure will be apparent to those skilled in the art from consideration of the specification and practice of the invention disclosed herein. It is intended that the specification and examples be considered as exemplary only, with the claims being entitled to their full breadth of scope, including equivalents.

What is claimed is:

1. A method comprising:
sensing magnet presence information and magnet orientation information for each magnet position of a plurality of magnet positions on a cannula mounted to a manipulator arm of a surgical system, the manipulator arm configured to manipulate movement of a surgical instrument mounted at the manipulator arm and the cannula configured to receive the surgical instrument in a mounted state at the manipulator arm,
the magnet presence information indicating a presence or absence of a magnet at the magnet position, and
the magnet orientation information indicating an orientation of a magnet present at the magnet position; and
automatically determining identification information about the cannula based on a combination of the magnet presence information and the magnet orientation information for all magnet positions of the plurality of magnet positions.

2. The method of claim 1, wherein:
each magnet position of the plurality of magnet positions has a corresponding dedicated sensor of a plurality of sensors; and
sensing magnet presence information for each magnet position of the plurality of magnet positions comprises using each corresponding dedicated sensor of the plurality of sensors to sense magnetic field strength.

3. The method of claim 2, wherein:
sensing magnet presence information indicating presence of a magnet comprises sensing the magnetic field strength exceeding a threshold; and
sensing magnet presence information indicating absence of a magnet comprises sensing magnetic field strength not exceeding a threshold.

4. The method of claim 2, wherein:
each magnet position of the plurality of magnet positions has a corresponding dedicated sensor of a second plurality of sensors; and
sensing magnet orientation information for each magnet position of the plurality of magnet positions comprises using each corresponding dedicated sensor of the second plurality of sensors to sense magnetic field orientation.

5. The method of claim 2, wherein:
sensing magnet orientation information comprises using the plurality of sensors to sense magnetic field orientation.

6. The method of claim 2, wherein:
the plurality of sensors and the plurality of magnet positions are arranged such that in a state of the cannula mounted to the surgical system each magnet position of the plurality of magnet positions is in sensing proximity to its corresponding dedicated sensor.

7. The method of claim 6, wherein:
the plurality of magnet positions is arranged in a first planar array at the cannula;
the plurality of sensors is arranged in a second planar array at the surgical system; and
the second planar array is complementary to the first planar array.

8. The method of claim 2, wherein:
the plurality of sensors comprises one or more omni-polar magnetic sensors.

9. The method of claim 1, wherein:
all magnet positions of the plurality of magnet positions have a corresponding dedicated sensor group of a plurality of sensor groups; and
sensing magnet presence information for each magnet position of the plurality of magnet positions comprises using each corresponding dedicated sensor group of the plurality of sensor groups to sense magnetic field strength.

10. The method of claim 9, wherein:
sensing magnet orientation information comprises using the plurality of sensor groups to sense magnetic field orientation.

11. The method of claim 10, wherein:
each sensor group of the plurality of sensor groups comprises one or more presence sensors to detect magnetic field strength and one or more orientation sensors to detect magnetic field orientation.

12. The method of claim 10, wherein:
each sensor group of the plurality of sensor groups comprises a first orientation sensor to sense a first magnetic field having a first orientation and a second orientation sensor to sense a second magnetic field having a second orientation.

13. The method of claim 10, wherein:
one or more sensor groups of the plurality of sensor groups comprises a single sensor to detect both magnetic field strength and magnetic field orientation.

14. The method of claim 9, wherein:
the plurality of sensor groups and the plurality of magnet positions are arranged on the surgical system such that in a state of the cannula mounted to the surgical system each magnet position of the plurality of magnet positions is in sensing proximity to its corresponding dedicated sensor group.

15. The method of claim 14, wherein:
the plurality of magnet positions is arranged in a first planar array at the cannula;
the plurality of sensor groups is arranged in a second planar array at the surgical system; and
the second planar array is complementary to the first planar array.

16. The method of claim 9, wherein:
one or more sensor groups of the plurality of sensor groups comprises an omni-polar magnetic sensor.

17. The method of claim 1, wherein:
the method further comprises automatically assigning a first value, a second value, or a third value for each magnet position of the plurality of magnet positions based on the sensing;

the first value corresponds to a magnet with a first orientation being present at the magnet position;
the second value corresponds to a magnet with a second orientation being present at the magnet position; and
the third value corresponds to absence of a magnet at the magnet position.

18. The method of claim 17, wherein:
a combination of the first, second, and third values assigned for all magnet positions of the plurality of magnet positions encodes an identifier of the cannula; and
automatically determining the identification information about the cannula comprises determining the identifier.

19. The method of claim 18, wherein:
automatically determining the identification information about the cannula further comprises searching a storage medium for property information associated with a plurality of types of cannula based on the identifier.

20. The method of claim 19, wherein:
the property information comprises one or more of cannula type, cannula shape, cannula length, cannula diameter, and cannula material.

21. The method of claim 1, wherein:
the identification information about the cannula comprises at least one of a cannula type, a cannula shape, a cannula length, a cannula diameter, and a cannula material.

22. The method of claim 1, wherein:
the method further comprises automatically determining a mismatch in response to the identification information not matching expected identification information.

23. The method of claim 22, wherein:
the method further comprises providing feedback to a user of the surgical system in response to the mismatch.

24. The method of claim 23, wherein:
the method further comprises preventing use of the manipulator arm of the surgical system in response to determining the mismatch.

25. A method comprising:
sensing magnet presence information and magnet orientation information for each magnet position of a plurality of magnet positions on a cannula mounted to a surgical system,
the magnet presence information indicating a presence or absence of a magnet at the magnet position, and
the magnet orientation information indicating an orientation of a magnet present at the magnet position; and
automatically determining identification information about the cannula based on a combination of the magnet presence information and the magnet orientation information for all magnet positions of the plurality of magnet positions;
wherein each magnet position of the plurality of magnet positions has a corresponding dedicated sensor of a plurality of sensors; and
sensing magnet orientation information for each magnet position of the plurality of magnet positions comprises using each corresponding dedicated sensor of the plurality of sensors to sense an angle between a predetermined reference direction and a magnetic field orientation.

* * * * *